(12) United States Patent
Altman

(10) Patent No.: US 7,998,105 B2
(45) Date of Patent: *Aug. 16, 2011

(54) METHOD OF TREATING CORONARY ARTERIES WITH PERIVASCULAR DELIVERY OF THERAPEUTIC AGENTS

(75) Inventor: Peter A. Altman, South San Francisco, CA (US)

(73) Assignee: BioCardia, Inc., San Carlos, CA (US)

( * ) Notice: Subject to any disclaimer, the term of this patent is extended or adjusted under 35 U.S.C. 154(b) by 1071 days.

This patent is subject to a terminal disclaimer.

(21) Appl. No.: 10/671,270

(22) Filed: Sep. 24, 2003

(65) Prior Publication Data

US 2004/0102759 A1    May 27, 2004

Related U.S. Application Data

(60) Division of application No. 10/353,117, filed on Jan. 27, 2003, now abandoned, which is a continuation of application No. 09/407,461, filed on Sep. 28, 1999, now Pat. No. 6,511,477, which is a continuation-in-part of application No. 09/177,765, filed on Oct. 23, 1998, now Pat. No. 6,443,949, which is a continuation-in-part of application No. 08/816,850, filed on Mar. 13, 1997, now Pat. No. 6,086,582.

(51) Int. Cl.
*A61N 1/30* (2006.01)

(52) U.S. Cl. .......................................................... 604/19

(58) Field of Classification Search ................. 600/407; 623/1.11, 1.42; 604/19, 48, 500; 606/194; 128/898

See application file for complete search history.

(56) References Cited

U.S. PATENT DOCUMENTS

| | | | |
|---|---|---|---|
| 4,146,029 A | 3/1979 | Ellinwood, Jr. | 128/260 |
| 4,797,285 A | 1/1989 | Barenholz et al. | 424/450 |
| 4,871,549 A | 10/1989 | Ueda et al. | |
| 4,891,223 A | 1/1990 | Ambegaonkar et al. | |
| 5,190,761 A | 3/1993 | Liburdy | 424/450 |
| 5,236,424 A | 8/1993 | Imran | |
| 5,246,707 A | 9/1993 | Haynes | 424/450 |
| 5,275,819 A | 1/1994 | Amer et al. | 424/408 |
| 5,324,325 A | 6/1994 | Moaddeb | 607/120 |
| 5,387,419 A | 2/1995 | Levy et al. | 424/422 |
| 5,439,446 A * | 8/1995 | Barry | 604/103.01 |
| 5,443,495 A * | 8/1995 | Buscemi et al. | 623/1.21 |

(Continued)

FOREIGN PATENT DOCUMENTS

JP          2069414          3/1990

(Continued)

OTHER PUBLICATIONS

Miller et al., Degradation Rates of Oral Resorbable Implants (Polylactates and Polyglycolates): Rate Modification and Changes in PLA/PFA Copolymer Ratios, II J. Biomed. Mater. Res. 711-719 (1977).

(Continued)

*Primary Examiner* — Tse Chen
*Assistant Examiner* — Jacqueline Cheng
(74) *Attorney, Agent, or Firm* — K. David Crockett, Esq.; Crockett & Crockett, PC

(57) ABSTRACT

A method of treating the intraluminal disease in a coronary artery by injecting therapeutic agents perivascularly into the myocardium near the site of disease.

37 Claims, 7 Drawing Sheets

U.S. PATENT DOCUMENTS

| | | | | |
|---|---|---|---|---|
| 5,510,077 A * | 4/1996 | Dinh et al. | 264/485 |
| 5,527,344 A | 6/1996 | Arzbaecher et al. | 607/3 |
| 5,551,427 A | 9/1996 | Altman | 128/642 |
| 5,634,895 A | 6/1997 | Igo et al. | 604/21 |
| 5,637,113 A * | 6/1997 | Tartaglia et al. | 623/1.42 |
| 5,662,929 A | 9/1997 | Lagace et al. | 424/450 |
| 5,681,278 A | 10/1997 | Igo et al. | 604/52 |
| 5,690,682 A | 11/1997 | Buscemi et al. | 607/3 |
| 5,700,486 A | 12/1997 | Canal et al. | 424/501 |
| 5,759,573 A | 6/1998 | Kim | 424/450 |
| 5,824,341 A | 10/1998 | Seth et al. | |
| 5,843,089 A * | 12/1998 | Sahatjian et al. | 623/1.11 |
| 5,914,345 A | 6/1999 | Slepian et al. | 514/496 |
| 5,928,669 A | 7/1999 | Davis et al. | 424/489 |
| 5,981,568 A * | 11/1999 | Kunz et al. | 514/411 |
| 6,080,728 A * | 6/2000 | Mixson | 514/44 |
| 6,086,582 A | 7/2000 | Altman et al. | 606/41 |
| 6,087,107 A | 7/2000 | Sheffield et al. | 435/6 |
| 6,099,561 A * | 8/2000 | Alt | 623/1.44 |
| 6,110,490 A | 8/2000 | Thierry | 424/450 |
| 6,152,141 A * | 11/2000 | Stevens et al. | 128/898 |
| 6,156,029 A | 12/2000 | Mueller | 606/15 |
| 6,199,554 B1 | 3/2001 | Mann et al. | 128/898 |
| 6,306,125 B1 | 10/2001 | Parker et al. | 604/117 |
| 6,346,099 B1 | 2/2002 | Altman | 604/164.01 |
| 6,379,931 B1 * | 4/2002 | Rossi et al. | 435/91.31 |
| 6,709,427 B1 * | 3/2004 | Nash et al. | 604/508 |
| 2002/0019350 A1 * | 2/2002 | Levine et al. | 514/12 |
| 2002/0122792 A1 * | 9/2002 | Stegmann | 424/94.1 |
| 2003/0171294 A1 * | 9/2003 | Hung et al. | 514/12 |

FOREIGN PATENT DOCUMENTS

| | | |
|---|---|---|
| JP | 7053835 | 2/1995 |
| JP | 7196477 | 8/1995 |
| JP | 9503488 | 4/1997 |
| JP | 10504300 | 4/1998 |
| WO | WO9503036 | 2/1995 |
| WO | PCT/CA96/00725 | 10/1996 |

OTHER PUBLICATIONS

Wang et al, pH-Sensitive Immunoliposomes Mediate Target-cell-specific Delivery and Controlled Expression of a Foreign Hene in Mouse, 84 Proc. Nat. Acad. Sci. 7851 (Nov. 1987).

Putney et al., Improving Protein Therapeutics with Sustained-Release Formulations, 16 Nature Biotechnology 153-57 (Feb. 1998).

Kibat et al., Enzymatically Activated Microencapsulated Liposomes Can Provide Pulsatile Drug Release, 4 FASEB Journal 2533 (May 1990).

Chu et al., pH Sensitive Liposomes, 4 Journal of Liposome Rsearch 361-395 (1994).

Liu et al., Role of Cholesterol in the Stability of pH Sensitive, Large Unilamellar Liposomes Prepared by the Detergent-Dialysis Method, 981 Biochem. Biophys. L. Act., 254-60 (1989).

Miller, Lymphatics of the Heart, Raven Press, New York (1982).

Scheinman et al., Supraventricular Tachyarrhythmias: Drug Therapy Versus Catheter Ablation, 17 Clin. Cardiol. II-11 (1994).

Wang et al., Highly Efficient DNA Delivery Mediated by pH-Sensitive Immunoliposomes, 28 Biochemistry 9508 (1989).

Gerasimov, et al., Triggered Release from Liposomes Mediated by Physically and Chemically Induced Phase Transitions, Vesicles, Edited by Morton Rosoff, Marcel Dekker, Inc., New York (1996).

Lazarus et al., Comparative Effects of Basic Fibroblast Growth Factor and Vascular Endothelial Growth Factor on Coronary Collateral Development and the Arterial Response to Injury, 94 Circulation 1074-1082 (Sep. 1996).

Lin et al., Expression of recombinant Genes in Myocardium in Vivo After Direct Injection of DNA, 82 Circulation 2217-2221 (Dec. 1990).

French et al., Direct in Vivo Gene Transfer into Porcine Myocardium Using Replication Deficient Adenoviral Vectors, 90 Circulation 2414-2424 (Nov. 1994).

Mulhauser et al., Safety and Efficacy of in Vivo Gene Transfer into the Porcine Heart with Replication-deficient, Recombinant Adenovirus Vectors, 3 Gene Therapy 145-153 (1996).

March et al., Biodegradable Microspheres Containing a Colchicine Analogue Inhibit DNA Synthesis in Vascular Smooth Muscle Cells, 89 Circulation 1929-1933 (May 1994).

Arras et al., The Delivery of Angiogenic Factors to the Heart by Microsphere Therapy, 16 Nature Biotechnology (Feb. 1998).

* cited by examiner

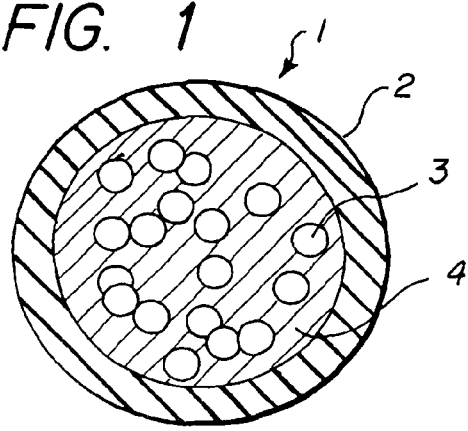
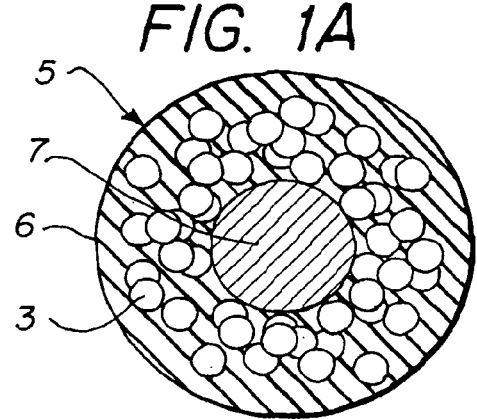
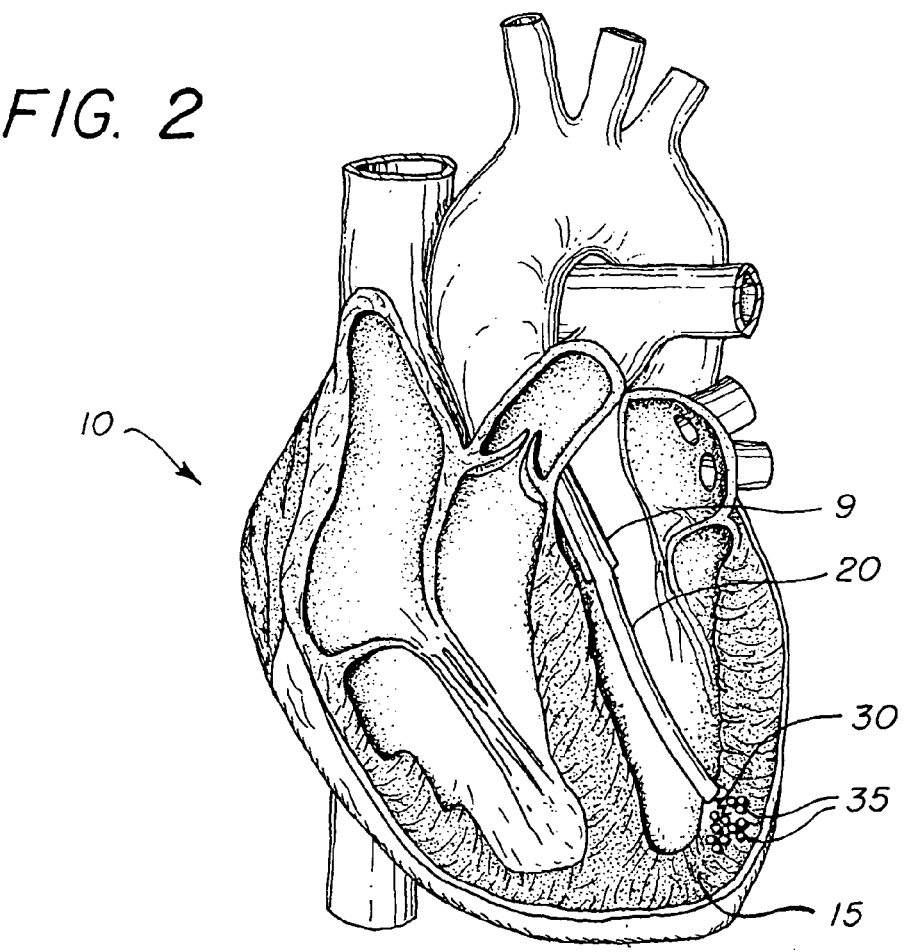

TIME = t1

TIME = t2

TIME = t3

TIME = t4

METHOD OF TREATING CORONARY ARTERIES WITH PERIVASCULAR DELIVERY OF THERAPEUTIC AGENTS

This application divisional application of U.S. App. Ser. No. 10/353,117 filed Jan. 27, 2003 now abandoned, which is a continuation of U.S. App. Ser. No. 09/407,461 file Sep. 28, 1999, now U.S. Pat. No. 6,511,477, which is a continuation-in-part of U.S. App. Ser. No. 09/177,765 filed Oct. 23, 1998, now U.S. Pat. No. 6,443,949, which is a continuation-in-part of U.S. App. Ser. No. 08/816,850 filed Mar. 13, 1997, now U.S. Pat. No. 6,086,582.

FIELD OF THE INVENTION

The present invention relates to the interstitial delivery of particulate drug delivery systems for large and small molecule therapeutic agents within the heart.

BACKGROUND OF THE INVENTION

Local drug delivery provides many advantages. Approaches for local controlled release of agents at a depth within a tissue such as the heart, pancreas, esophagus, stomach, colon, large intestine, or other tissue structure to be accessed via a controllable catheter will deliver drugs to the sites where they are most needed, reduce the amount of drug required, increase the therapeutic index, and control the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives.

Local drug delivery to the heart is known. In U.S. Pat. No. 5,551,427, issued to Altman, implantable substrates for local drug delivery at a depth within the heart are described. The patent shows an implantable helically coiled injection needle which can be screwed into the heart wall and connected to an implanted drug reservoir outside the heart. This system allows injection of drugs directly into the wall of the heart acutely by injection from the proximal end, or on an ongoing basis by a proximally located implantable subcutaneous port reservoir, or pumping mechanism. The patent also describes implantable structures coated with coating which releases bioactive agents into the myocardium. This drug delivery may be performed by a number of techniques, among them infusion through a fluid pathway, and delivery from controlled release matrices at a depth within the heart. Controlled release matrices are drug polymer composites in which a pharmacological agent is dispersed throughout a pharmacologically inert polymer substrate. Sustained drug release takes place via particle dissolution and slowed diffusion through the pores of the base polymer. Pending applications Ser. No. 08/816,850 by Altman and Altman, and Ser. No. 09/057,060 by Altman describes some additional techniques for delivering pharmacological agents locally to the heart. Implantable drug delivery systems, such as controlled release matrices, have been well described in the literature, as has the use of delivering particulate delivery systems or particulate drug carriers such as microcapsules, lipid emulsions, microspheres, nanocapsules, liposomes, and lipoproteins into the circulating blood. However, local delivery of such micro drug delivery systems to a depth within the myocardium using endocardial catheter delivery and epicardial injection systems have not been described, and have many advantages that have not been foreseen.

Recently, local delivery to the heart has been reported of therapeutic macromolecular biological agents by Lazarous [Circulation, 1996, 94:1074-1082.], plasmids by Lin [Circulation, 1990; 82:2217-2221], and viral vectors by French [Circulation, Vol. 90, No 5, November 1994, 2414-2424] and Muhlhauser [Gene Therapy (1996) 3, 145-153]. March [Circulation, Vol. 89, No 5, May 1994, 1929-1933.] describes the potential for microsphere delivery to the vessels of the heart, such as to limit restenosis, and this approach has also been used for the delivery of bFGF by Arras [Margarete Arras et. al., The delivery of angiogenic factors to the heart by microsphere therapy, Nature Biotechnology, Volume 16, February 1998.] These approaches for microsphere delivery obstruct flow, and will be delivered preferentially to capillary beds which are well perfused. Further, these approaches do not deliver therapeutic agents to the interstitial spaces. None of this work recognizes the potential to use particulate drug delivery system to optimize local drug delivery at a depth within the myocardium. This art also does not recognize the potential such delivery systems have in treating disease substrates in the myocardium if delivered to an appropriate region of the myocardial interstitium.

Problems exist for delivering small molecules or lipophilic molecules which rapidly transport through the capillary wall, to well-perfused tissues such as the myocardium. These problems are due to the convective losses of the agents to the systemic circulation. By going rapidly across the capillary wall, the small molecules are rapidly carried away by the bloodstream. Local delivery of an easily transported molecule is difficult because local delivery concentrations are rapidly reduced at very small distances from the delivery site due to convective losses. Such easily transported agents cannot treat an effective area of tissue locally without raising the systemic concentrations of the agents to a therapeutic level.

SUMMARY

The therapeutic compounds described below comprise very small capsules which can be injected into body tissue, particularly the heart. The capsules include an encapsulating layer which surrounds a therapeutic agent. After injection, the encapsulating layer degrades or dissolves, and the therapeutic agent is released within the heart. The therapeutic agent may be one of any number of known agents such as anti-arrhythmic drugs, gene therapy solutions, and macromolecules intended to have either acute or long-term effects on the heart. While some of these therapeutic agents are used to treat the heart by injecting them into the heart, they are of such small size that they readily enter the cardiac capillary system and the cardiac lymphatic system, and are quickly transported away from the injection site. Thus, in prior treatment methods, relatively large doses and repeated doses are required to provide therapeutic effect at the injection site. To provide a solution to this problem, the capsules described below are provided in sizes that are too large to permit capillary transport or lymphatic transport. Thus, injected capsules are immobile within the heart tissue, and upon degradation they will release a therapeutic agent very near the site of injection. The capsules may also be provided in sizes that are too large to permit capillary transport, but small enough to enter the lymphatic system and be transported away from the injection site in the cardiac lymphatic system, so that the therapeutic effect is provided at some distance from the injection site. The encapsulating layer may be made from various materials including biodegradable polymers in the form of microspheres, or from standard vesicle forming lipids which form liposomes and micelles.

BRIEF DESCRIPTION OF THE DRAWINGS

FIG. 1 illustrates an encapsulated therapeutic agent designed for injection into the heart.

FIG. 1a illustrates a microsphere encapsulated therapeutic agent designed for injection into the heart.

FIG. 2 illustrates a method for injection of therapeutic agents into the heart.

DETAILED DESCRIPTION OF THE INVENTION

Figure 3:
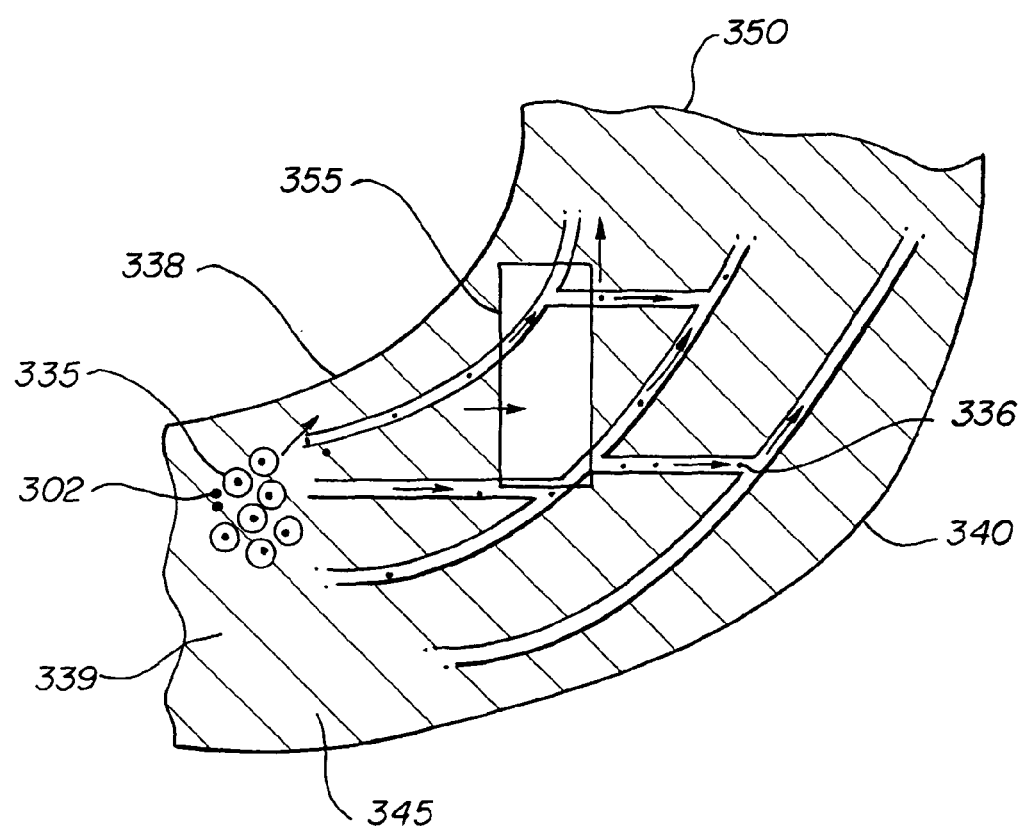
FIG. 3 illustrates the expected transportation of molecules released from degrading microspheres injected within the myocardium.

FIG. 1 illustrates a microdrug delivery system which is comprised of a compound or substance for use in delivering a therapeutic agent to the heart. The compound is comprised of numerous capsules 1 which are made up of an encapsulating layer 2 which may form a microsphere formulated from Prolease™ or other biodegradable microsphere material, or from vesicle forming lipids which may form a liposome or micelle, and a therapeutic agent 3 within the encapsulating layer. Therapeutic agent may be embedded in a biodegradable polymer, or in a carrier fluid 4. The encapsulating layer is typically pharmacologically inactive, although techniques to make it active to promote cellular uptake and/or receptor binding are known in the art. The therapeutic agent may be any of a wide variety of drugs and other compounds used for treatment of various ailments of the heart. The capsules are carried within a solution such as pH controlled saline to create a slurry which can be injected into the heart of a patient. Prior to injection, the encapsulating layer will protect the macromolecule from mechanical and chemical degradation within the catheter or needle used for injection. Once injected into the heart tissue, the size of the encapsulating layer will inhibit transport of the compound away from the injection site, either through the cardiac capillary system and/or the cardiac lymphatic system. Also once injected, the encapsulating layer will degrade, either due to chemical conditions, biological conditions, or temperature conditions within the heart wall, and release the encapsulated molecule. The time period over which the encapsulating layer degrades is variable, depending upon its formulation, such formulations being available in the art. The half-life for degradation may be selected from several minutes to several days, depending on the therapy intended. Thus a sustained reservoir of therapeutic agent is created within the heart tissue near the injection site, and therapeutic agents are slowly released near the injection site to treat nearby tissue. The need to flood the entire heart and/or the entire blood system of the patient is eliminated, so that very small doses of therapeutic agents are enabled. This reduces the cost of treatment, and minimizes the otherwise harsh side effects associated with many effective therapeutic agents.

FIG. 1a illustrates the formulation of the microdrug delivery system from a microsphere formulated from Prolease™, biodegradable polymers, or particulate controlled release matrix with molecules of therapeutic agent dispersed throughout the microsphere. The microsphere 5 in FIG. 1a includes numerous molecules or particles of therapeutic agents 3 dispersed throughout the solid biodegradable microsphere or particulate controlled release matrix 6. As the microsphere material degrades, therapeutic agents are slowly released from the microsphere. This formulation differs from the capsule formulation, but may be employed to achieve similar results. In one preferred embodiment, the core 7 of the solid biodegradable microsphere contains no therapeutic drug at a radius less then approximately 20 um, preferably about 15 um. Thus the core of the microsphere, to a radius of up to 20 um, preferably 15 um, may be devoid of therapeutic agent. Alternatively, the core of the microsphere, to a radius of up to 10 um, preferably 7.5 um, may be devoid of therapeutic agent. This prevents problems associated with migration of the potentially potent depot within the lymphatic system. The core of the microsphere may also be designed to have a longer degradation half-life so that essentially all of the drug will be delivered before the microsphere can substantially migrate through the lymphatic networks. Thus, the particulate micro delivery systems includes millispheres, microspheres, nanospheres, nanoparticles, liposomes and micelles, cellular material and other small particulate controlled release structures which can be advanced in a fluid suspension or slurry and be delivered to a depth within the heart muscle. These small drug delivery systems may deliver therapeutic agents as diverse as small molecule antiarrhythmics, agents that promote angiogenesis, and agents that inhibit restenosis. They may also be combined in cocktails with steroid agents such as dexamethasome sodium phosphate to prevent inflammatory response to the implanted materials. Separate particulate drug delivery systems for delivering different agents to the same region of the heart may also be used. The release kinetics of separate micro delivery systems may also be different.

Delivery of small drug delivery systems reduce the likelihood of causing embolic events in the brain, kidneys, or other organs should these drug delivery systems escape into the left chambers of the heart. Because the systems are small only very small arterioles would be occluded should one of them escape into the blood within the left chambers of the heart. This is not a problem in the right side of the heart, as the lungs act as a filter of potentially embolic materials.

FIG. 2 shows a catheter system 9 with centrally located drug delivery catheter 20 implanted at a depth within the left ventricular apex 15 of the heart 10. Hollow penetrating structure 30 has penetrated the heart muscle, and has transported particulate encapsulated agents 35 such as VEGF, bFGF, or other therapeutic agent to a depth within the heart muscle. The encapsulated agents are injected into the heart muscle (the myocardium) in an intact portion of the heart muscle (that is, not into a vessel such as the ventricle chamber, a coronary artery or a TMR channel which are subject to blood flow and immediate transport of the injected particles from the area). The capsules or microspheres are suspended within a fluid inside the catheter to facilitate injection. The use of small drug delivery systems in slurry or suspension delivered by a fluidic pathway (a needle or catheter) to a depth within the myocardium can solve different problems in pharmacokinetics of local cardiovascular drug delivery. Such an approach can provide for well controlled and easily administered sustained dosage of therapeutic macromolecules, eliminate the issue of convective losses of small molecules for local delivery, and increase the ability of gene therapy preparations to gain access through the cell membrane.

Problems exist for macromolecular therapies in the heart such as short half-lives and the presence of endogenous inhibitors. Many macromolecular therapies may be improved by providing a sustained dosage over time to overcome endogenous inhibitors, as well as encapsulation to protect the macromolecule from degradation.

The interstitial (intramuscular or intra-myocardial) delivery of particulate drug delivery systems for sustained release such as biodegradable microspheres solves these problems. Particulate systems, such as microspheres, enable the time course of delivery and area of treatment to be controlled. In addition, such particulate systems may be delivered to the target site by a fluid pathway within a drug delivery catheter such as those described in the prior art. The advantages of these particulate delivery systems is that they are implanted at a depth within the heart tissue and the implanted catheter device can be removed immediately. Thus, a very quick procedure may be performed on an outpatient basis to deliver particulate drug delivery systems to a depth within a patient's heart for sustained delivery measured in days to weeks.

The microspheres to be used in this treatment are manufactured to be large enough to prevent migration within the myocardial interstitium, but also small enough to be deliverable by a catheter fluid pathway to a depth with the myocardium. Microspheres such as Alkerme's (Cambridge, Mass.) Prolease system enable freeze dried protein powder to be homogenized in organic solvent and sprayed to manufacture microspheres in the range of 20 to 90 um (microns). Development of such microsphere depots for sustained release of proteins with unaltered integrity requires methods to maintain stability during purification, storage, during encapsulation, and after administration. Many of these techniques have been recently summarized in the literature. See, e.g., Scott D. Putney, and Paul A. Burke: Improving protein therapeutics with sustained release formulations, Nature Biotechnology, Volume 16, February 1998, 153-157. Issues associated with degradation for biodegradable polymers used in such microspheres are also well known [Robert Miller, John Brady, and Duane E. Cutright: Degradation Rates of Oral resorbable Implants {Polylactates and Polyglycolates}: Rate Modification and Changes in PLA/PGA Copolymer Ratios, J. Biomed. Mater. Res., Vol. II, PP. 711-719 (1977). The value of delivering microsphere encapsulated macromolecular agents such as proteins bFGF and VEGF to a depth within the heart muscle for controlled release have not been described, and have substantial unrecognized benefits over other delivery approaches.

FIG. 3 shows a schematic description of microsphere encapsulated agents for delivery. Macromolecule angiogenic agents 336 such as VEGF and bFGF are delivered with biodegradable microspheres 335 in combination with biodegradable microspheres 302 enclosing dexamethasone sodium phosphate or other anti inflammatory steroid. In other embodiments the anti-inflammatory agents may be combined with a particular therapeutic within the same encapsulation. The microspheres are injected through the endocardium 338 and into the myocardium 339 so that they reside interstitially within the heart tissue. Both microspheres 335 and 302 are too large to be transported away by either the capillary system or the lymphatic system from the injection site within the myocardium. Where the microspheres are greater than about 15 micrometers in diameter, they will remain at the injection site and will not migrate. Where the microspheres have a diameter less than about 1 micrometer they will migrate in the cardiac lymphatic system, but will not enter the cardiac capillary system. As the microspheres degrade over time, their components and the therapeutic molecules will be transported away from the injection site by the myocardial lymphatic system which has been described in relation to the transport of extravasated proteins from the endocardium 338 to the epicardium 340, and from the apex of the heart 345 towards the base of the heart 350. [Albert J. Miller, Lymphatics of the Heart, Raven Press, New York, 1982.] Here the microspheres are delivered endocardially and inferiorly (that is, upstream in the lymphatic system) to the region to be treated, identified here schematically by window 355. Clearly regions within window 355 and regions directly adjacent to the window will all result in effective delivery of agents to the desired target, and are viable approaches as well. The large molecules delivered in such a fashion will be transported through the lymphatics far more slowly than small molecules which would be more rapidly convected away from the delivery region by the blood supply. But approaches exist to minimize the issues associated with convective losses of small molecules.

The method of packaging the small molecule so that it cannot be convected away by the blood, yet will be distributed locally in the tissue, and then effecting its action on the tissue can be accomplished with liposomal encapsulation. The term "liposome" refers to an approximately spherically shaped bilayer structure, or vesicle, comprised of a natural or synthetic phospholipid membrane or membranes, and sometimes other membrane components such as cholesterol and protein, which can act as a physical reservoir for drugs. These drugs may be sequestered in the liposome membrane or may be encapsulated in the aqueous interior of the vesicle. Liposomes are characterized according to size and number of membrane bilayers. Vesicle diameters can be large (>200 nm) or small (<50 nm) and the bilayer can have unilamellar, oligolamellar, or multilamellar membrane.

Liposomes are formed from standard vesicle forming lipids, which generally include neutral and negatively charged phospholipids with or without a sterol, such as cholesterol. The selection of lipids is generally guided by considerations of liposome size and ease of liposome sizing, and lipid and water soluble drug release rates from the site of liposome delivery. Typically, the major phospholipid components in the liposomes are phosphatidylcholine (PC), phosphatidylglycerol (PG), phosphatidyl serine (PS), phosphatidylinositol (PI) or egg yolk lecithin (EYL). PC, PG, PS, and PI having a variety of acyl chains groups or varying chain lengths are commercially available, or may be isolated or synthesized by known techniques. The degree of saturation can be important since hydrogenated PL (HPL) components have greater stiffness than do unhydrogenated PL components; this means that liposomes made with HPL components will be more rigid. In addition, less saturated Pls are more easily extruded, which can be a desirable property particularly when liposomes must be sized below 300 nm.

Current methods of drug delivery by liposomes require that the liposome carrier will ultimately become permeable and release the encapsulated drug. This can be accomplished in a passive manner in which the liposome membrane degrades over time through the action of agents in the body. Every liposome composition will have a characteristic half-life in the circulation or at other sites in the body. In contrast to passive drug release, active drug release involves using an agent to induce a permeability change in the liposome vesicle. In addition, liposome membranes can be made which become destabilized when the environment becomes destabilized near the liposome membrane (Proc. Nat. Acad. Sci. 84, 7851 (1987); Biochemistry 28: 9508, (1989).) For example, when liposomes are endocytosed by a target cell they can be routed to acidic endosomes which will destabilize the liposomes and result in drug release. Alternatively, the liposome membrane can be chemically modified such that an enzyme is placed as a coating on the membrane which slowly destabilizes the liposome (The FASEB Journal, 4:2544 (1990). It is also well known that lipid components of liposomes promote peroxidative and free radical reactions which cause progressive degradation of the liposomes, and has been described in U.S. Pat. No. 4,797,285. The extent of free radical damage can be reduced by the addition of a protective agent such as a lipophilic free radical quencher is added to the lipid components in preparing the liposomes. Such protectors of liposome are also described in U.S. Pat. No. 5,190,761, which also describes methods and references for standard liposome preparation and sizing by a number of techniques. Protectors of liposomal integrity will increase the time course of delivery and provide for increased transit time within the target tissue.

Liposomal encapsulation of small molecules makes local delivery possible. By having a liposomal preparation which is unstable in the body, it will collapse after it is delivered. Liposomes can be constructed in varying size, including the size range less than 400 nm, preferably 200-250 nm. Between the time of delivery and the time of collapse, the liposomes in the size range less than 400 nm will be transported into and through the lymphatics and provide for redistribution of small molecules. Delivery of liposomes that degrade rapidly once delivered to the body in a matter of minutes goes against the typical approaches for liposomal delivery and design. Typically pH sensitive liposomes involves the destabilization of the liposome in the endosome as the pH falls from physiological 7.4 to 5.0, while here we are describing liposomes which become destabilized near pH 7.4. [Chun-Jung Chu and Francis C. Szoka: pH Sensitive Liposomes, Journal of Liposome Research, 4(1), 361-395 (1994)].

Figure 4A:
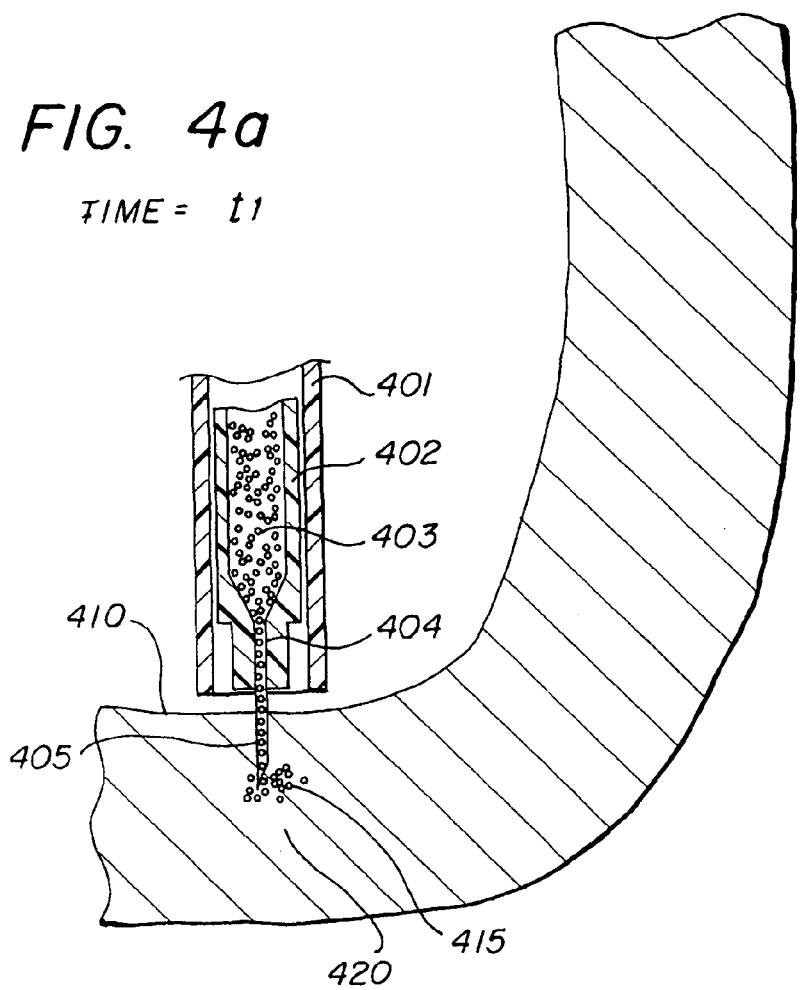
FIGS. 4a through 4d illustrate the progression of injected liposome encapsulated small molecules within the heart tissue after injection.
Figure 4B:
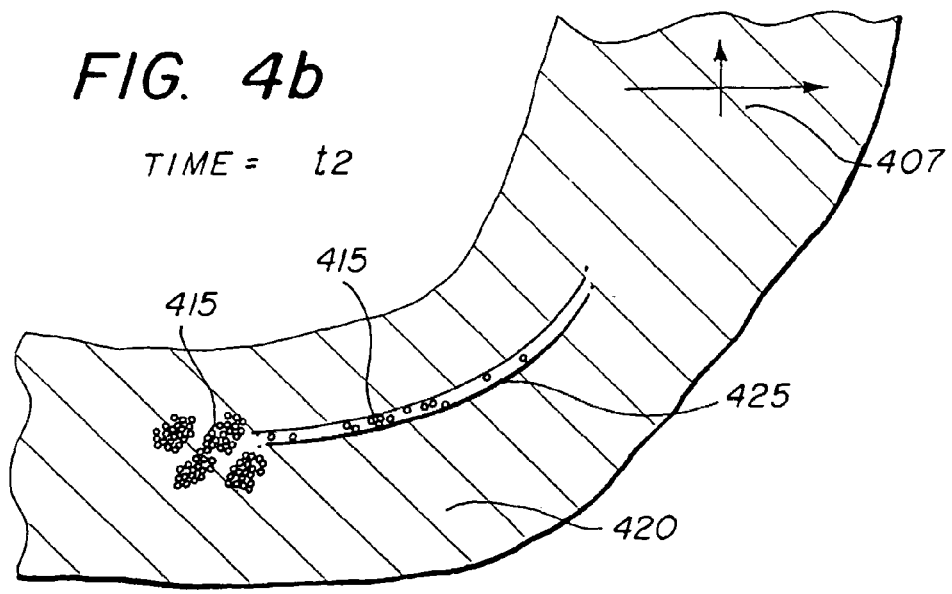
Figure 4C:
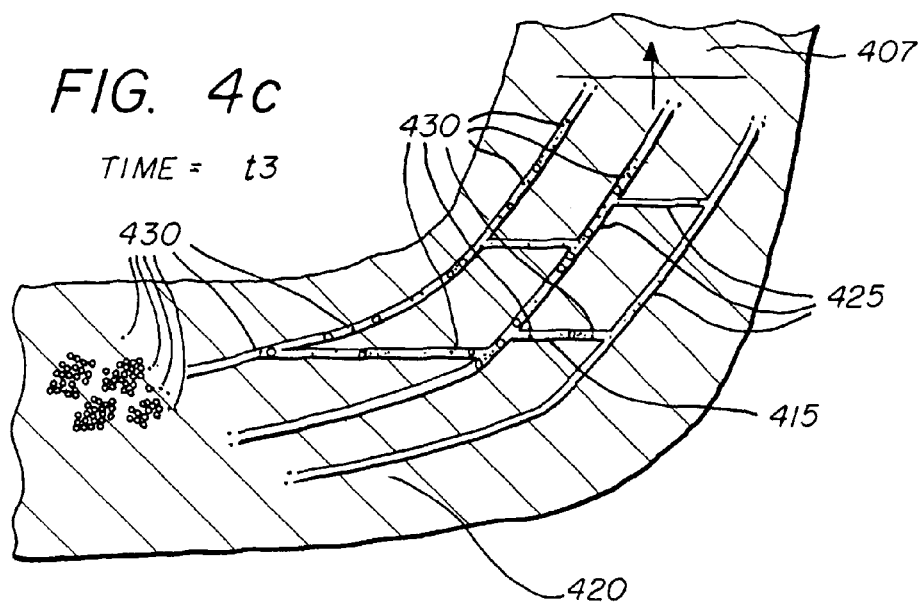
Figure 4D:
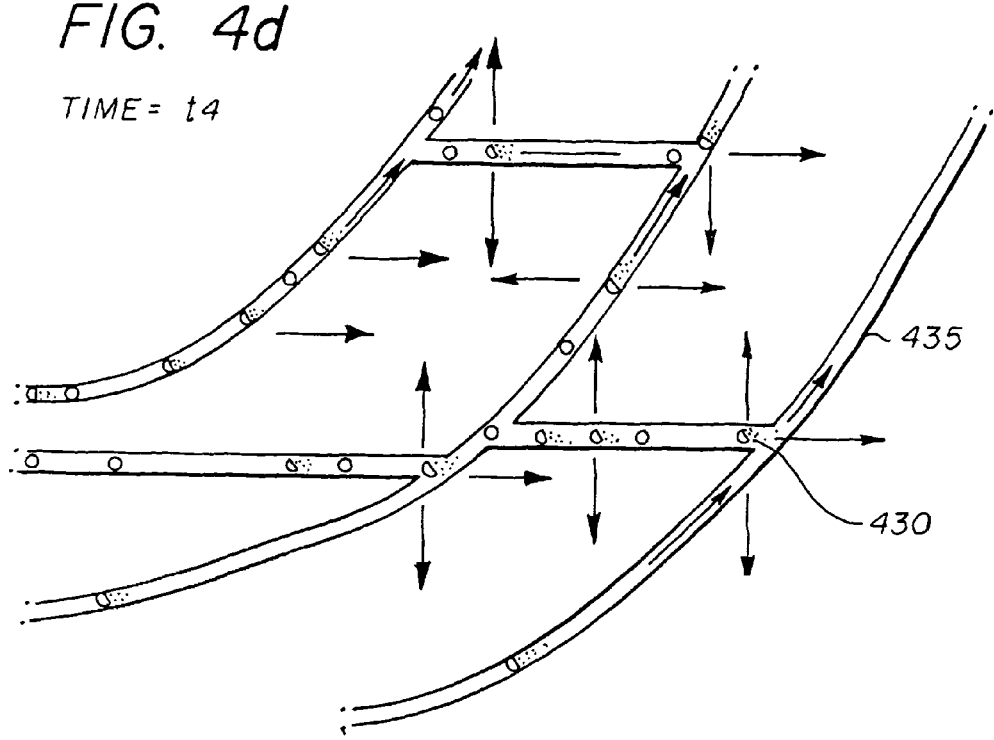

FIG. 4a shows a schematic of the delivery of small molecules within liposomes which are unstable at physiological pH (the pH of the heart tissue or the physiological environment into which the molecules are delivered). A guiding catheter 401 is shown with a single lumen needle drug delivery catheter 402 containing liposome encapsulated small molecules 403 which are delivered through needle 404 by way of needle fitting 404. Here the penetrating needle 405, crosses the endocardium 410 to deliver liposomes 415 to a depth within the heart wall 420. Although the liposomes could be various sizes and have a number of lipid bilayers, in the preferred embodiment they are small unilamellar liposome vesicles (SUVs) to augment their rapid uptake by the cardiac lymphatic system. The drug delivery catheter 402 contains liposomes bathed in a solution at their stable pH so that they do not collapse prematurely. FIG. 4b shows that the catheter has been removed and that the uptake of the SUVs 415 by a lymphatic vessel 425 at some time t2 later than the time they were delivered t1 to the myocardial interstitium, such as the subendocardial interstitium. Of course, other physiochemical properties could be used such that the liposomal preparations are delivered from a system in which they are stable to a system at a depth within the heart with different physio-chemical properties in which they are unstable. Temperature is another possible property that could be varied. Arrows near 407 show that lymphatic transport is from endocardium to epicardium and from apex to base in the heart. The lymphatic transport will carry the encapsulated small molecules a distance which will be governed by their stability and mean time to liposomal degradation. FIG. 4c shows the same tissue in a larger view at time t3 later than time t2 in which SUVs 415 are degrading and releasing small molecule drugs 430 within the lymphatics. The spread of the released drug in the degraded liposomes 430 provides therapeutic treatment to a large region of heart tissue while systemic effects are minimized. FIG. 4d shows that upon degradation, the small molecules 430 will be transported through the lymphatic vessel wall 435 to the adjacent myocytes, and be convected rapidly away from the region. This transport through the lymphatic walls is shown schematically by the large arrows at the site of the degraded liposome with released small molecules. Because of the inability of the small molecules to be convected away rapidly until the liposome collapses, a much larger region of tissue will be able to be treated locally than by local infusion of the small molecules themselves. In one embodiment, oleic acid (OA) and dioleoylphosphatidyl-ethanolamine (DOPE) devoid of cholesterol which have been shown to be extremely unstable in the presence of body fluid plasma [Liu, D. and Huang, L., *Role Of Cholesterol In The Stability Of pH Sensitive, Large Unilamellar Liposomes Prepared By The Detergent-Dialysis Method*, Biochim Biophys. Act, 981, 254-260 (1989)] and could be used to encapsulate small molecule gene regulators such as hormones or antiarrhythmic agents.

In another embodiment, liposomes of dimyristoylphosphatidylcholine (DMPC) or dipalmitoylphosphatidylcholine (DPPC), cholesterol (CHOL) and dicetylphosphate (DCP) containing Amiodarone are prepared at pH 4.5 using DMPC:CHOL:DCP (3:1:2 mol ratio) and are stable at this pH, and are less stable at the neutral pH of the heart. Because the stability of the liposome can be varied, and even triggered by external inputs, a specific size of tissue may be treated locally with small molecules in this fashion.

If the small molecule has a very short half-life, or antagonists have been delivered systematically to prevent the drug from having systemic effects, such an approach will enable local delivery of small molecules to regions of varying sizes within the myocardium. Alternatively, some small molecules may be delivered transiently only when needed, such as to terminate a cardiac arrhythmia, and so that systemic effects are minimized. Such systems could involve a permanently implantable infusion system for either continuous or transient local delivery as has been described in the art.

Liposomal encapsulated agents delivered to the myocardium will also provide advantages to other therapeutic agents. Liposomal encapsulation can improve transfection of gene therapy preparations, and cytosolic delivery of macromolecules. Liposomal delivery systems can be used to alter macromolecule and gene therapy pharmacokinetics and improve their ability to enter the cell cytosol. Delivery vehicles capable of delivering agents to the cell cytosol have been created in fusogenic liposomes, which enable them to cross the cell membrane in a lipophilic vesicle. Newer techniques for triggering the liposomes so that their contents may be released within the cytosol have been developed, and a brief review of this work has appeared in the literature [Oleg Gerasimov, Yuanjin Rui, and David Thompson, "Triggered release from liposomes mediated by physically and chemically induced phase transitions", in Vesicles, edited by Morton Rosoff, Marcel Dekker, Inc., New York, 1996.] Because the liposome is not stable at the physicochemical conditions within the body, it can be designed to degrade in a time period less than it takes to get to the cardiac lymph node. Once the liposome is degraded, the body can address the liposomal contents and break them up. Liposomes within the systemic circulation can then be minimized, as will endocytosis of the macromolecules and gene therapy preparations outside the target region. No approach for delivering such liposomal encapsulated agents to a depth within the myocardium has been described.

As described, the endocardial to epicardial, and apex to base lymphatic transport pathways can be used to deliver macromolecules and particulate drug delivery systems to the targeted region in need of therapy. The increased risk of ischemia in the subendocardium implies that it is the tissue in need of therapeutic intervention. This has been hypothesised as being due to the higher interstitial pressures during cardiac systole, which may limit perfusion of this tissue region as opposed to subepicardial tissue. In order to treat this region with therapeutic agents from a locally delivered depot site, delivery should be such that endogenous transport pathways deliver agents to the target regions. This can be accomplished by delivering agents on the endocardial side of the ischemic zone, and towards the apex of the heart. Such an approach has not been previously described. The internal lymphatic system of the heart can also be used to control delivery of the therapeutic agents throughout the heart. For example, liposome encapsulated or micelle encapsulated amiodarone, or other anti-arrhythmic agents can be injected into the ventricle wall, (and the liposomes formulated for a half life of about five minutes to sixty minutes), whereupon the lymphatic system will transport the liposomes upward toward the atrium of the heart to the vicinity of the cardiac lymph node. Lymphatic vessels flow adjacent to the atrium of the heart, such that agents delivered into the ventricular wall will migrate to the atrium and the atrium wall. This transport happens within minutes, so that the release of the therapeutic molecules will occur in the walls of the atrium. This has potential for treating atrial arrhythmias. (Thus it can be appreciated that variation of the size of the encapsulated therapeutic agent can be employed in remarkable new therapies.)

The agents to be delivered may include small molecules, macromolecules, and gene therapy preparations. These will be briefly defined.

"Small molecules" may be any smaller therapeutic molecule, known or unknown. Examples of known small molecules relative to cardiac delivery include the antiarrhythmic agents that affect cardiac excitation. Drugs that predominantly affect slow pathway conduction include digitalis, calcium channel blockers, and betablockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propefenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Melvin: Supraventricular Tachycardia: Drug Therapy Versus Catheter Ablation, Clinical Cardiology Vol. 17, Supp. II-11-II-15 (1994).] Many other small molecule agents are possible, such as poisonous or toxic agents designed to damage tissue that have substantial benefits when used locally such as on a tumor. One example of such a small molecule to treat tumors is doxarubicin.

A "macromolecule" is any large molecule and includes proteins, nucleic acids, and carbohydrates. Examples of such macromolecules include the growth factors, Vascular Endothelial Growth Factor, basic Fibroblastic Growth Factor, and acidic Fibroblastic Growth Factor, although others are possible. Examples of macromolecular agents of interest for local delivery to tumors include angiostatin, endostatin, and other anti-angiogenic agents.

A "gene therapy preparation" is broadly defined as including genetic materials, endogenous cells previously modified to express certain proteins, exogenous cells capable of expressing certain proteins, or exogenous cells encapsulated in a semi-permeable micro device. This terminology is stretched beyond its traditional usage to include encapsulated cellular materials as many of the same issues of interstitial delivery of macrostructures apply.

The term "genetic material" generally refers to DNA which codes for a protein, but also encompasses RNA when used with an RNA virus or other vector based upon RNA. Transformation is the process by which cells have incorporated an exogenous gene by direct infection, transfection, or other means of uptake. The term "vector" is well understood and is synonymous with "cloning vehicle." A vector is non-chromosomal double stranded DNA comprising an intact replicon such that the vector is replicated when placed within a unicellular organism, for example by a process of transformation. Viral vectors include retroviruses, adenoviruses, herpesvirus, papovirus, or otherwise modified naturally occurring viruses. Vector also means a formulation of DNA with a chemical or substance which allows uptake by cells. In addition, materials could be delivered to inhibit the expression of a gene. Approaches include: antisense agents such as synthetic oligonucleotides which are complimentary to RNA or the use of plasmids expressing the reverse compliment of a gene, catalytic RNA's or ribozymes which can specifically degrade RNA sequences, by preparing mutant transcripts lacking a domain for activation, or over express recombinant proteins which antagonize the expression or function of other activities. Advances in biochemistry and molecular biology in recent years have led to the construction of recombinant vectors in which, for example, retroviruses and plasmids are made to contain exogenous RNA or DNA respectively. In particular instances the recombinant vector can include heterologous RNA or DNA by which is meant RNA or DNA which codes for a polypeptide not produced by the organism susceptible to transformation by the recombinant vector. The production of recombinant RNA and DNA vectors is well understood and need not be described in detail.

Many delivery systems could be used to deliver these agents to a region of the myocardial interstitium. During surgical procedures, a syringe may suffice, but it is more likely that a transvascular delivery catheter such has been called out would be used to deliver the appropriate therapeutic agents to the appropriate sites. Essentially, a steerable catheter would be advanced to a location within the heart chamber and placed adjacent to the heart wall. The drug delivery catheter would be advanced so that it penetrates the heart wall and the desired volume of particulate delivery slurry or suspension (0.05 ml to 2.0 ml) would be infused. The penetrating structure would be disengaged, and the drug delivery catheter would be pulled back a short distance within the delivery catheter. The steerable catheter would be repositioned, and the process may be repeated a number of times if so desired.

The benefits of the different controlled systems may also be combined. For example, to provide for local small molecule delivery that is sustained over time, and does not require an indwelling drug delivery system in the heart chamber, the SUV liposomes containing the small molecules could be delivered within biodegradable microdrug delivery systems such as larger more stable liposomes or other fully encapsulated controlled release system, such as a biodegradable impermeable polymer coatings. The time course of release is governed then by the additive time delay of the barriers that separate the therapeutic agent from the host, as well as their combined transport pathways. Microsphere delivery systems could also be used.

Figure 5:
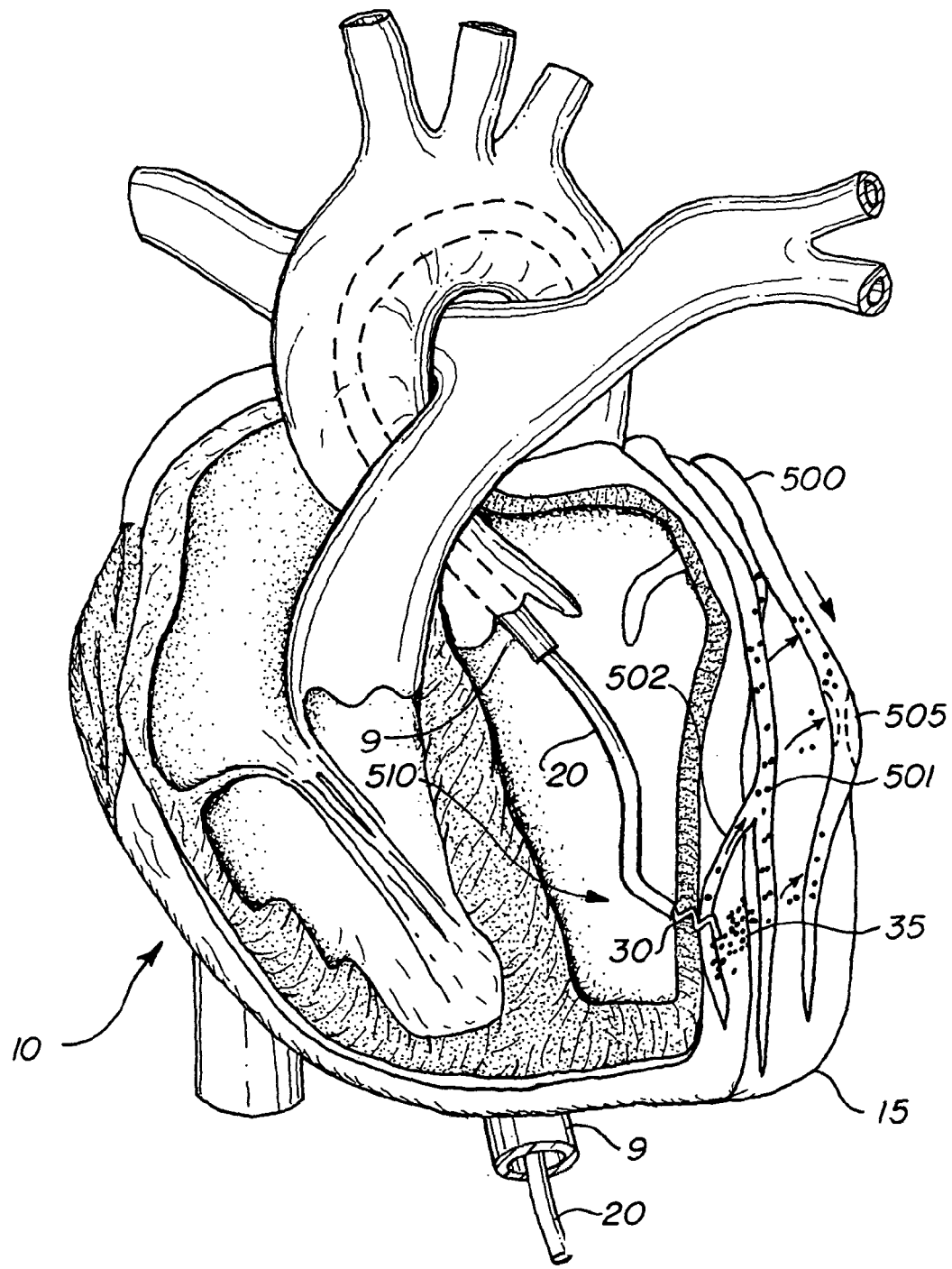
FIG. 5 illustrates a method of delivering therapeutic agents to the coronary arteries through the lymphatic vessels.
Figure 6:
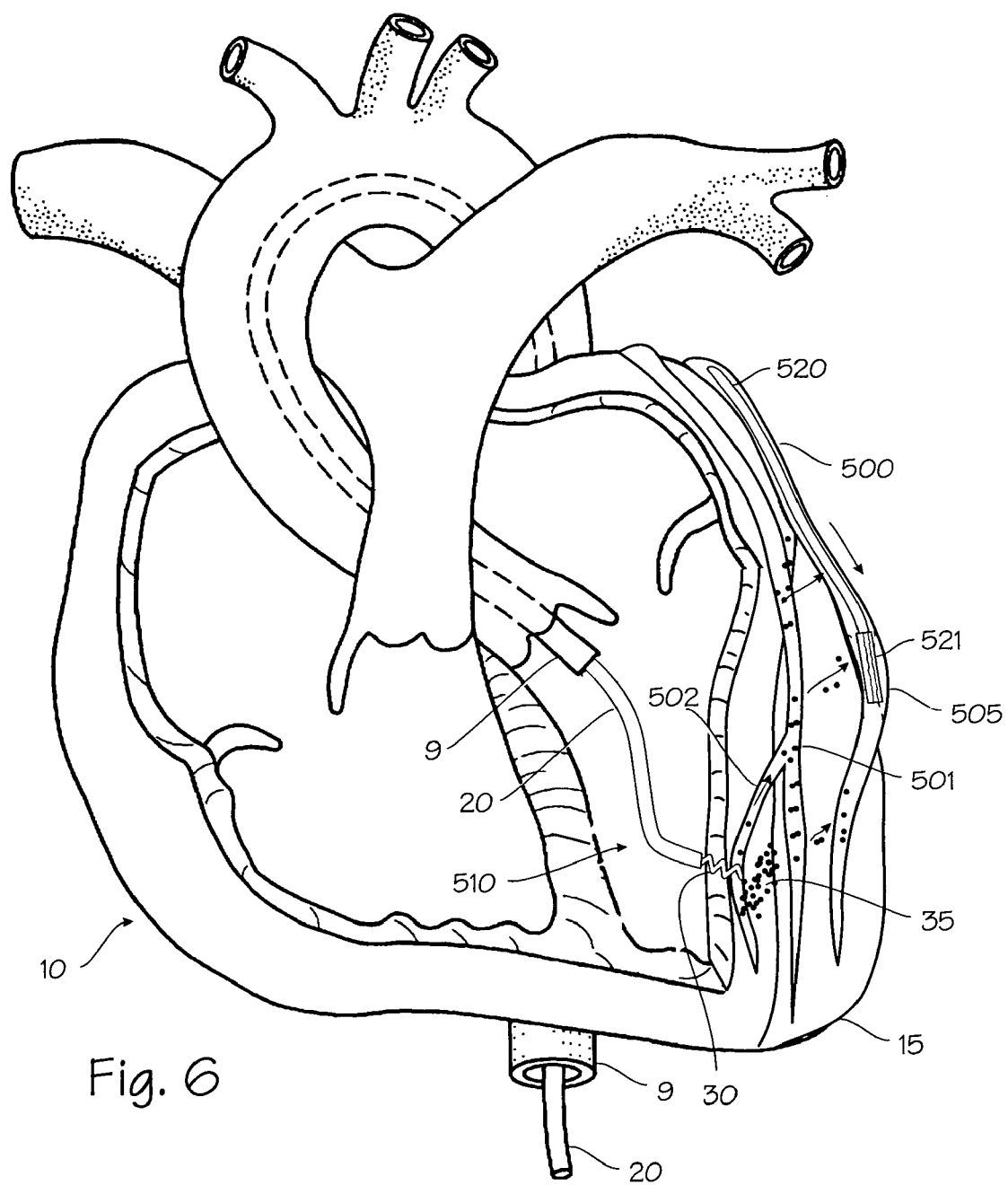
FIG. 6 is a like view showing the balloon angioplasty.
Figure 7:
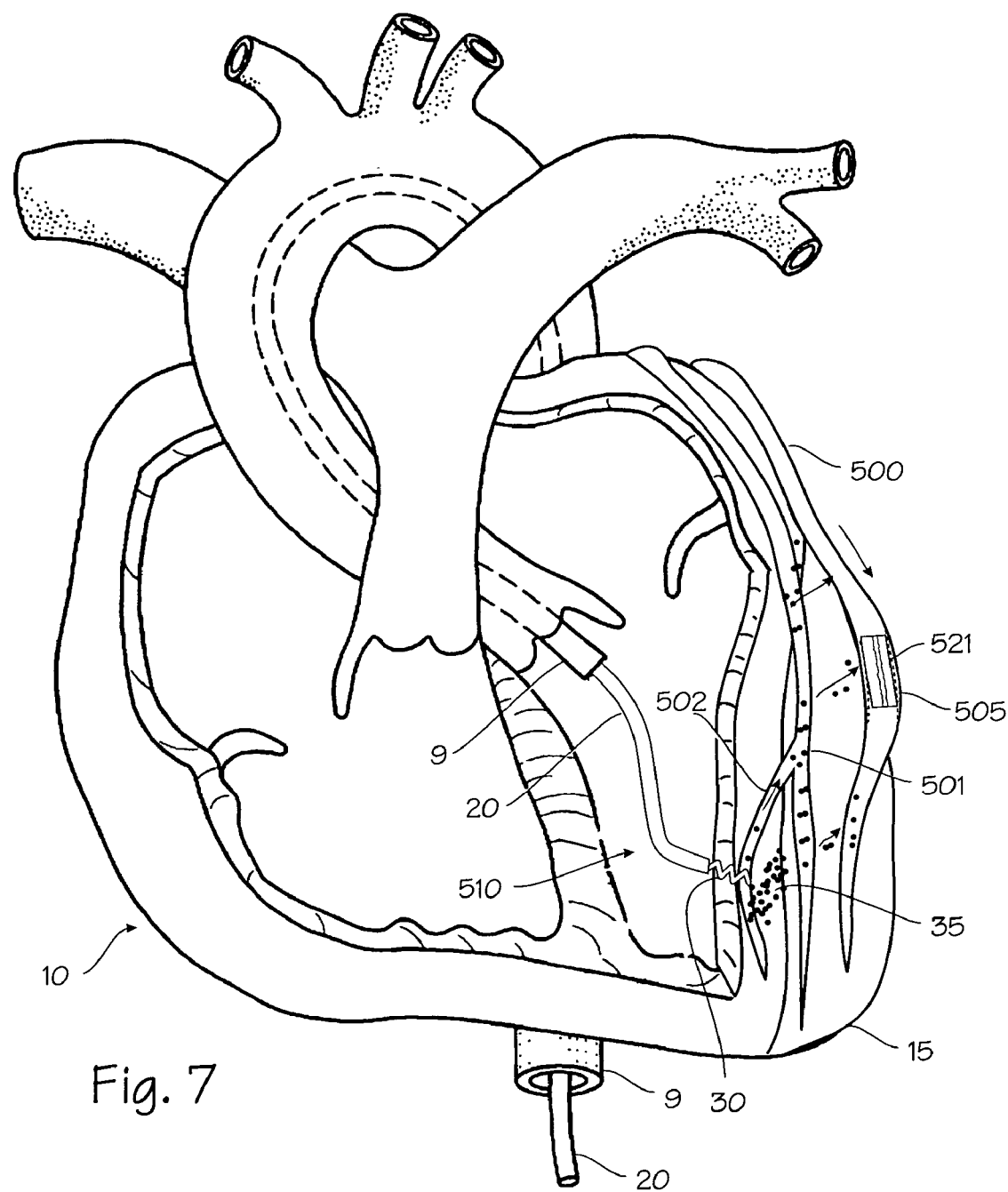
FIG. 7 is a like view showing a deployed stent.

The ability to deposit therapeutic agents in to the myocardium for uptake into the cardiac lymphatic system, combined with the ability of some of the molecules discussed above to migrate from the lymphatic ducts into parallel running arteries, permits introduction of therapeutic agents for the coronary arteries to be introduced through this pathway. The result is a very low flow environment for the introduction of anti-stenotic compounds and other arterial therapeutic agents, as compared to the infusion of therapeutic agents into the high flow environment of the coronary arteries themselves. The method illustrated in FIG. 5 is useful to deliver therapeutic agents to the coronary arteries, such as the left coronary artery and its branches, including the left anterior descending coronary artery, and the right coronary artery and its branches. As illustrated in FIG. 5, catheter system 9 with centrally located drug delivery catheter 20 implanted at a depth within the left ventricular apex 15 of the heart 10. Hollow penetrating structure 30 has penetrated the heart muscle from the endocardial side. The artery to be treated, in this case the circumflex branch of the left coronary artery 500, courses over the surface of the heart (chosen for illustration purposes only). A corresponding epicardial lymphatic vessel 501 runs nearby, and many sub-epicardial lymphatic vessel such as vessel 502 drain into the epicardial lymphatic vessel. (It should be noted that the cardiac lymphatic vessels are both numerous and largely uncharted, and may be highly variable from person to person). The artery is occluded by an arterial plaque, cholesterol or stenotic mass 505 which is amendable to treatment with drug therapies. The artery may have been previously treated with angioplasty, or a stent may have been placed across the occlusion. For example, balloon angioplasty is illustrated in FIG. 6, which shows an angioplasty catheter 520 with a balloon 521 mounted its distal tip, placed within the artery 500 in the area of a lesion (mass 505, for example). Expansion the lesion with the angioplasty balloon may precede treatment with catheter 510. Likewise, as illustrated in FIG. 7, a stent 530 may be placed within the region of the blood vessel occluded by a lesion (mass 505, for example). Both methods of treatment are often accompanied by injury to the surrounding blood vessel and restenosis. In any case, several drugs are available to either ameliorate the blockage or prevent restenosis or re-occlusion after balloon angioplasty and/or stent placement. The delivery catheter is navigated into the endocardial space of the left ventricle 510, and secured in place with penetrating structure 30. A small dose of therapeutic agent, indicated by the molecules 35, is injected into the myocardium, and the penetrating structure is withdrawn. (Withdrawal of the penetrating structure may be delayed as necessary to prevent the therapeutic agent from draining back into the ventricular space.) The molecules of the therapeutic agent are taken up by the lymphatic system, entering into vessels 501 and 502, and transported upwardly. The molecules also migrate out of the lymphatic system and then migrate into the nearby coronary artery, following multiple paths indicated by the arrows in FIG. 5. The molecules penetrate the adventicia, or outer layer, of the coronary artery, and thus enter the coronary artery. Molecules enter the coronary artery along the entire length that runs near the lymphatic vessels which initially take up the molecules. Thus, therapeutic agent enters the coronary blood vessel at the site of occlusion and proximally to the occlusion, after having been injected into a more distal location (relative to the coronary artery). The term entering the artery may include entering the arterial wall without entering the lumen of the artery, or passing through the arterial wall into the lumen of the artery. While the method is illustrated in relation to the left circumflex coronary artery, it may be used with all the coronary arteries. Also, while endocardial access is preferred for the method as applied to the coronary arteries located on the anterior surface of the heart (left and right coronary arteries). Therapeutic agents may be deposited into the myocardium through catheters delivered into the coronary sinus, the coronary veins, and even the coronary arteries, including the coronary artery subject to treatment by angioplasty or stent placement. Additionally, while it is preferable to accomplish the therapy percutaneously, the method may be accomplished by injection into the heart, epicardially, during open surgery, or during endoscopic or key-hole surgery through the chest.

Various therapeutic agents can be delivered to the coronary arteries using this approach. Anti-restenosis agents may include agents which inhibit smooth muscle proliferation, endothelial cell proliferation, and growth of other components of arterial plaque and stenosis, antioxidant drugs, anti-inflammatory drugs, platelet derived growth factor antagonists, and numerous other proposed compounds. Anti-restenosis agents also include anti-neoplastic agents such as taxol, statins (such as Lovastatin and Provastatin), Pemirolast, Tranilast, Cilostrazol, INOS, ENOS, ECNOS, and gene therapy formulations. All of these agents may be formulated as time-release or controlled release formulations for delivering these molecules by deposition in the myocardium in position for uptake and eventual migration into a target site in the coronary arteries. The therapeutic agents may be incorporated into biodegradable microspheres with a diameter larger than 15 um (and preferably greater that 50 um) in diameter so that a depot can be placed distal to the region of the vessel where treatment is desired for sustained delivery to the target vessel for extended periods, such as several hours or several of weeks. The microspheres would elute agents into the myocardium slowly over a period of time in order to enable the sustained delivery through the lymphatics of the heart. In many cases the molecules may be linked to other molecules such as carbohydrates to prevent their intravasation and convective losses to the blood. The microspheres, which are sized to restrict their migration, degrade within the myocardium near the deposition site and release agents which then migrate through the lymphatics and migrate from the lymphatics to the adventicia and cells within the vascular wall within the target region of the coronary vessel. For other therapies, gene therapy preparations are delivered to infect the cardiac myocytes in order to transfect the RNA for production of the therapeutic proteins locally which will then migrate through the lymphatic walls to treat the target vessel peri-adventicially.

The microspheres used in this method are preferably sized to inhibit migration and immediate uptake by the lymphatic vessels, and are preferably 50 um in diameter and greater, but perhaps as small as 30 um. Agents could be encapsulated in liposomal structures with diameters ranging from 50 to 600 nm which are transported by the lymphatics and designed to break up at physiological pH such that agents are released which are able to diffuse through the lymphatic and arterial walls.

Anti-angiogenic agents could also be used to limit the angiogenic response which has been recently associated in the literature with atherosclerotic plaques. The hypothesis that anti-angiogenic agents may limit restenosis could be used during a revascularization procedure in which angiogenic agents are delivered along with anti-angiogenic agents at the time of stent placement. By having the anti-angiogenic agents be the first delivered they would transport through the lymphatics and to the region of injury caused by balloon angioplasty or stent placement and minimize the restenosis. Although the reservoir of microspheres containing angiogenic agents may be delivered at the same catheterization procedure used to accomplish angioplasty to stent placement, and potentially at the same location, they would be released after the anti-angiogenic and anti-neoplastic agents have had their effect for limiting restenosis. Thus dosage forms for anti-angiogenic agents and angiogenic agents could be placed in the heart simultaneously. One way of doing this would be to have a microsphere in which the core contains angiogenic agents and the outer shell contains anti-angiogenic agents. Another method of doing this is to supply anti-angiogenic agents in solution or in small microspheres which are immediately taken up in the lymphatic vessels, while supplying the angiogenic agents in larger microspheres which will not be taken up. The method thus comprises treating a coronary blood vessel with stent placement, balloon angioplasty, or both, and delivering a dose of therapeutic agent to the site of treatment, where the therapeutic agent is delivered to the myocardium at a location distal to the site of treatment, and the therapeutic agent includes anti-angiogenic agent to be released in a time frame shortly after treatment and angiogenic agent to be released in a time frame after release of the anti-angiogenic agent. Alternately, the anti-angiogenic agent can be delivered to the target site with the angioplasty balloon or stent, by coating the balloon or stent with the anti-angiogenic agent, while the angiogenic agent is deposited in the myocardium for delayed transport to the target site.

Thus, the method allows the use of the lymphatic vessels and endogenous lymphatic transport to carry agents from the myocardially located depot of therapeutic agents to the target coronary arteries such that agents are delivered through the target vessel walls peri-adventicially. This provides a means of delivering therapeutic agents peri-adventitially to the vessels of the heart that is far superior to surgical placement of a peri-adventitial controlled release devices, and delivery of agents to the space between the pericardial space between the parietal and visceral pericardium.

While the inventions have been described in relation to the treatment of cardiac tissue, it should be appreciated that the compounds and methods of treatment may be applied to various body tissues. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of treating a stenosis or restenosis in a coronary blood vessel characterized by a proximal end nearest the origination of blood flow from the heart and a distal end, said method comprising the steps of:
   implanting a stent at a first location within the coronary blood vessel; and
   injecting a therapeutic agent comprising an anti-restenosis agent into the myocardium proximate the coronary blood vessel at a second location, where the second location is distal, in relation to the coronary blood vessel, to the first location.

2. The method of claim 1 further comprising the steps of: injecting the therapeutic agent into the myocardium from an endocardial space of the heart.

3. The method of claim 1 further comprising the steps of: injecting the therapeutic agent peri-adventitially through the blood vessel wall.

4. The method of claim 1 further comprising the step of: injecting the therapeutic agent peri-adventitially through a coronary vein or coronary sinus.

5. The method of claim 1, 2, 3 or 4 further comprising the steps of:
   selecting the anti-restenosis agent from the group comprising anti-oxidant drugs, anti-inflammatory drugs, anti-neoplastic agents, anti-angiogenic agents and gene therapy agents.

6. The method of claim 1, 2, 3 or 4 further comprising the step of:
   providing the therapeutic agent in a time release formulation.

7. The method of claim 1, 2, 3 or 4 further comprising the step of:
   providing the therapeutic agent in a microsphere formulation.

8. The method of claim 1, 2, 3 or 4 further comprising the step of:
   providing the therapeutic agent in a formulation in which the therapeutic agent is encapsulated in micelles.

9. The method of claim 1, 2, 3 or 4 further comprising the step of:
   providing the therapeutic agent in a formulation in which the therapeutic agent is encapsulated in liposomes.

10. A method of treating a stenosis or restenosis in a coronary blood vessel characterized by a proximal end nearest the origination of blood flow from the heart and a distal end, said method comprising the steps of:
    performing an angioplasty procedure at a first location within the coronary blood vessel; and
    injecting a therapeutic agent comprising an anti-restenosis agent into the myocardium proximate the coronary blood vessel at a second location, where the second location is distal, in relation to the coronary blood vessel, to the first location.

11. The method of claim 10 further comprising the steps of: injecting the therapeutic agent into the myocardium from an endocardial space of the heart.

12. The method of claim 10 further comprising the steps of: injecting the therapeutic agent peri-adventitially through the blood vessel wall.

13. The method of claim 10 further comprising the step of: injecting the therapeutic agent peri-adventitially through a coronary vein or coronary sinus.

14. The method of claim 10, 11, 12 or 13 further comprising the steps of:
    selecting the anti-restenosis agent from the group comprising anti-oxidant drugs, anti-inflammatory drugs, anti-neoplastic agents, anti-angiogenic agents and gene therapy agents.

15. The method of claim 10, 11, 12 or 13 further comprising the step of:
    providing the therapeutic agent in a time release formulation.

16. The method of claim 10, 11, 12 or 13 further comprising the step of:
    providing the therapeutic agent in a microsphere formulation.

17. The method of claim 10, 11, 12 or 13 further comprising the step of:
    providing the therapeutic agent in a formulation in which the therapeutic agent is encapsulated in micelles.

18. The method of claim 10, 11, 12 or 13 further comprising the step of:
    providing the therapeutic agent in a formulation in which the therapeutic agent is encapsulated in liposomes.

19. A method of treating a segment of a coronary blood vessel, the segment characterized by a proximal end nearest the origination of blood flow from the heart and a distal end, said method comprising the steps of:

injecting a therapeutic agent comprising an anti-restenosis agent into the myocardium proximate the coronary blood vessel at a site distal, to the segment to be treated.

20. The method of claim 19 further comprising the steps of: injecting the therapeutic agent into the myocardium from an endocardial space of the heart.

21. The method of claim 19 further comprising the steps of: injecting the therapeutic agent peri-adventitially through the blood vessel wall.

22. The method of claim 19 further comprising the step of: injecting the therapeutic agent peri-adventitially through a coronary vein or coronary sinus.

23. The method of claim 19, 20, 21 or 22 further comprising the steps of:

selecting the anti-restenosis agent from the group comprising anti-oxidant drugs, anti-inflammatory drugs, anti-neoplastic agents, anti-angiogenic agents and gene therapy agents.

24. The method of claim 19, 20, 21 or 22 further comprising the step of:

providing the therapeutic agent in a time release formulation.

25. The method of claim 19, 20, 21 or 22 further comprising the step of:

providing the therapeutic agent in a microsphere formulation.

26. The method of claim 19, 20, 21 or 22 further comprising the step of:

providing the therapeutic agent in a formulation in which the therapeutic agent is encapsulated in micelles.

27. The method of claim 19, 20, 21 or 22 further comprising the step of:

providing the therapeutic agent in a formulation in which the therapeutic agent is encapsulated in liposomes.

28. A method of treating a segment of a coronary blood vessel characterized by an intraluminal disease, the segment further characterized by a proximal end nearest the origination of blood flow from the heart and a distal end, said method comprising the steps of:

injecting a therapeutic agent into the myocardium proximate the coronary blood vessel at a site distal, to the segment to be treated.

29. The method of claim 28 further comprising the steps of: injecting the therapeutic agent into the myocardium from an endocardial space of the heart.

30. The method of claim 28 further comprising the steps of: injecting the therapeutic agent peri-adventitially through the blood vessel wall.

31. The method of claim 28 further comprising the step of: injecting the therapeutic agent peri-adventitially through a coronary vein or coronary sinus.

32. The method of claim 28, 29, 30 or 31 further comprising the steps of:

selecting the therapeutic agent from the group comprising anti-oxidant drugs, anti-inflammatory drugs, anti-neoplastic agents, anti-angiogenic agents and gene therapy agents.

33. The method of claim 28, 29, 30 or 31 further comprising the step of:

providing the therapeutic agent in a time release formulation.

34. The method of claim 28, 29, 30 or 31 further comprising the step of:

providing the therapeutic agent in a microsphere formulation.

35. The method of claim 28, 29, 30 or 31 further comprising the step of:

providing the therapeutic agent in a formulation in which the therapeutic agent is encapsulated in micelles.

36. The method of claim 28, 29, 30 or 31 further comprising the step of:

providing the therapeutic agent in a formulation in which the therapeutic agent is encapsulated in liposomes.

37. A kit for delivering a therapeutic agent to a patient suffering from vascular disease characterized by a diseased treatment region in a coronary blood vessel, the diseased treatment region characterized by a proximal end nearest the origination of blood flow from the heart and a distal end, said kit comprising:

a catheter having means for introducing a therapeutic agent into in a perivascular space surrounding the blood vessel; and a dose of therapeutic agent suitable for introduction into the perivascular space surrounding the blood vessel through the catheter;

instructions for use of the catheter according to the following method:

positioning the means for introducing into the perivascular space; and delivering a dose of the therapeutic agent into the perivascular space near the diseased treatment region at a site distal, to the diseased treatment region.

* * * * *